US010692370B2

(12) United States Patent
Elgie et al.

(10) Patent No.: US 10,692,370 B2
(45) Date of Patent: Jun. 23, 2020

(54) TRAFFIC OBSTRUCTION DETECTION

(71) Applicant: INRIX INC., Kirkland, WA (US)

(72) Inventors: Judith Rosalyn Elgie, Manchester (GB); Dominic Jordan, Manchester (GB)

(73) Assignee: INRIX, Inc., Kirkland, WA (US)

( * ) Notice: Subject to any disclaimer, the term of this patent is extended or adjusted under 35 U.S.C. 154(b) by 507 days.

(21) Appl. No.: 15/122,750

(22) PCT Filed: Feb. 27, 2015

(86) PCT No.: PCT/US2015/017941
§ 371 (c)(1),
(2) Date: Aug. 31, 2016

(87) PCT Pub. No.: WO2015/134311
PCT Pub. Date: Sep. 11, 2015

(65) Prior Publication Data
US 2017/0076227 A1 Mar. 16, 2017

Related U.S. Application Data

(60) Provisional application No. 61/946,962, filed on Mar. 3, 2014.

(51) Int. Cl.
*G08G 1/00* (2006.01)
*G01C 21/28* (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC ....... G08G 1/096791; G08G 1/096811; G08G 1/0962; G08G 1/012; G08G 1/0112;
(Continued)

(56) References Cited

U.S. PATENT DOCUMENTS 5,250,946 A * 10/1993 Stanzcyk ............. G08G 1/0104
340/936
6,131,064 A 10/2000 Vieweg
(Continued)

OTHER PUBLICATIONS

EP Search Report cited in EP Application No. 15758511.8 dated Feb. 6, 2018, 6 pgs.
(Continued)

*Primary Examiner* — Brandon S Cole
(74) *Attorney, Agent, or Firm* — Cooper Legal Group, LLC

(57) ABSTRACT

One or more techniques and/or systems are provided for training and/or utilizing a traffic obstruction identification model for identifying traffic obstructions based upon vehicle location point data. For example, a training dataset, comprising sample vehicle location points (e.g., global positioning system location points of vehicles) and traffic obstruction identification labels (e.g., locations of known traffic obstructions such as stop signs, crosswalks, stop lights, etc.), may be evaluated to extract a set of training features indicative of traffic flow patterns. The set of training features and the traffic obstruction identification labels may be used to train a traffic obstruction identification model to create a trained traffic obstruction identification model. The trained traffic obstruction identification model may be used to determine whether a road segment has a traffic obstruction or not.

20 Claims, 7 Drawing Sheets

(51) Int. Cl.
| | |
|---|---|
| G08G 1/09 | (2006.01) |
| H04W 24/08 | (2009.01) |
| H04W 4/46 | (2018.01) |
| G08G 1/0967 | (2006.01) |
| H04W 4/50 | (2018.01) |
| G06N 20/00 | (2019.01) |
| G06F 16/29 | (2019.01) |
| H04W 4/024 | (2018.01) |
| H04W 4/029 | (2018.01) |
| G08G 1/01 | (2006.01) |
| B60W 40/08 | (2012.01) |
| B60W 40/09 | (2012.01) |
| G07B 15/06 | (2011.01) |
| G08G 1/0968 | (2006.01) |
| G08G 1/097 | (2006.01) |
| B60W 30/14 | (2006.01) |
| G05D 1/00 | (2006.01) |
| G07C 5/00 | (2006.01) |
| A61B 5/0205 | (2006.01) |
| A61B 5/0476 | (2006.01) |
| A61B 5/00 | (2006.01) |
| G05D 1/02 | (2020.01) |
| H04B 1/3822 | (2015.01) |
| H04L 29/08 | (2006.01) |
| B64C 39/02 | (2006.01) |
| H04B 7/185 | (2006.01) |
| G06Q 20/10 | (2012.01) |
| G06Q 30/02 | (2012.01) |
| H04W 12/08 | (2009.01) |
| H04M 15/00 | (2006.01) |
| G06Q 40/08 | (2012.01) |
| H04L 9/32 | (2006.01) |
| B60R 16/023 | (2006.01) |
| G07B 15/00 | (2011.01) |
| G08G 1/065 | (2006.01) |
| G01C 21/36 | (2006.01) |
| H04W 4/42 | (2018.01) |
| H04W 4/40 | (2018.01) |
| G01C 21/34 | (2006.01) |
| G08G 1/07 | (2006.01) |
| G08G 1/0962 | (2006.01) |
| G08G 1/0965 | (2006.01) |
| H04W 4/48 | (2018.01) |
| A61B 5/024 | (2006.01) |
| A61B 5/053 | (2006.01) |
| G06Q 50/30 | (2012.01) |

(52) U.S. Cl.
CPC ........ *A61B 5/4845* (2013.01); *B60R 16/0236* (2013.01); *B60W 30/143* (2013.01); *B60W 40/08* (2013.01); *B60W 40/09* (2013.01); *B64C 39/024* (2013.01); *G01C 21/3415* (2013.01); *G01C 21/3469* (2013.01); *G01C 21/3617* (2013.01); *G01C 21/3655* (2013.01); *G01C 21/3667* (2013.01); *G01C 21/3682* (2013.01); *G05D 1/0011* (2013.01); *G05D 1/0088* (2013.01); *G05D 1/021* (2013.01); *G06F 16/29* (2019.01); *G06N 20/00* (2019.01); *G06Q 20/102* (2013.01); *G06Q 30/0283* (2013.01); *G06Q 40/08* (2013.01); *G07B 15/00* (2013.01); *G07B 15/063* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/065* (2013.01); *G08G 1/07* (2013.01); *G08G 1/093* (2013.01); *G08G 1/097* (2013.01); *G08G 1/0962* (2013.01); *G08G 1/0965* (2013.01); *G08G 1/0967* (2013.01); *G08G 1/096725* (2013.01); *G08G 1/096741* (2013.01); *G08G 1/096775* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/024* (2018.02); *H04W 4/029* (2018.02); *H04W 4/40* (2018.02); *H04W 4/42* (2018.02); *H04W 4/50* (2018.02); *H04W 12/08* (2013.01); *A61B 5/024* (2013.01); *A61B 5/0531* (2013.01); *B60W 2040/0809* (2013.01); *B60W 2040/0872* (2013.01); *B60W 2540/22* (2013.01); *B60W 2552/00* (2020.02); *B60W 2555/20* (2020.02); *B60W 2710/1044* (2013.01); *B60W 2710/18* (2013.01); *B60W 2720/10* (2013.01); *B64C 2201/123* (2013.01); *G01C 21/3608* (2013.01); *G06Q 50/30* (2013.01); *G06Q 2240/00* (2013.01); *H04W 4/48* (2018.02)

(58) Field of Classification Search
CPC .......... H04W 4/42; H04W 4/50; H04W 4/40; A61B 5/02055; A61B 5/0476; A61B 5/4845; B60R 16/0236; B60W 30/143; B60W 40/08; B60W 40/09; B64C 39/024; G06Q 2240/00; G06Q 50/30; G06Q 30/0283; H04M 15/60; H04L 9/3247
USPC ..................................................... 706/1–62
See application file for complete search history.

(56) References Cited

U.S. PATENT DOCUMENTS

| | | | |
|---|---|---|---|
| 6,177,885 B1 | 1/2001 | Weil et al. | |
| 7,203,598 B1* | 4/2007 | Whitsell | G01C 21/26 340/988 |
| 7,398,076 B2* | 7/2008 | Kubota | G08G 1/096725 455/344 |
| 7,519,472 B1 | 4/2009 | Grigsby et al. | |
| 2005/0137786 A1* | 6/2005 | Breed | B60N 2/2863 701/482 |
| 2006/0092043 A1* | 5/2006 | Lagassey | G07C 5/008 340/907 |
| 2006/0106743 A1* | 5/2006 | Horvitz | G06N 99/005 706/21 |
| 2007/0052701 A1* | 3/2007 | Trotta | G06F 17/5004 345/419 |
| 2007/0208493 A1 | 9/2007 | Downs et al. | |
| 2008/0071465 A1* | 3/2008 | Chapman | G01C 21/3691 701/117 |
| 2009/0079586 A1* | 3/2009 | Bespalov | G08G 1/0104 340/905 |
| 2009/0292456 A1 | 11/2009 | Inoguchi et al. | |
| 2011/0144900 A1* | 6/2011 | Tennent | G01C 21/32 701/532 |
| 2011/0202266 A1 | 8/2011 | Downs et al. | |
| 2012/0109510 A1* | 5/2012 | Ota | B60W 30/188 701/400 |
| 2012/0274481 A1* | 11/2012 | Ginsberg | G08G 1/096775 340/905 |
| 2012/0307676 A1* | 12/2012 | Chan | H04W 24/08 370/252 |

(56) References Cited

U.S. PATENT DOCUMENTS

2013/0132434 A1* 5/2013 Scofield .............. G08G 1/0112
                                                707/771
2014/0005916 A1* 1/2014 Shen ................... G08G 1/0129
                                                701/119
2014/0114885 A1   4/2014 Han et al.

OTHER PUBLICATIONS

Corresponding International Application No. PCT/US15/17941, International Search report and written opinion dated Jun. 9, 2015.

* cited by examiner

TRAFFIC OBSTRUCTION DETECTION

CROSS-REFERENCE TO RELATED APPLICATIONS

This application claims priority to U.S. Provisional Patent Application No. 61/946,962 titled "DETERMINING HOV/HOT LANE TRAVEL TIMES", filed on Mar. 3, 2014, which is hereby incorporated by reference.

BACKGROUND

Many users utilize various devices to obtain route information. In an example, a user may utilize a smart phone to obtain walking directions to a nearby restaurant. In another example, a user may utilize a vehicle navigation device to obtain a map populated with driving directions to an amusement park. In a driving situation, a driver may want to view information that may affect an arrival time to a destination, such as traffic congestion and/or traffic obstructions (e.g., a stop light, a crosswalk, a stop sign, a railroad crossing, a traffic flow impediment, a permanent obstruction, etc.). Unfortunately, a navigation route provider may utilize map data that does not comprise points of interest for traffic flow such as traffic obstructions (e.g., the map data may not identify or list traffic obstructions). Identifying traffic flow by evaluating imagery of the map data, such as an aerial photo, may not provide an indication as to whether the traffic flow is a result of congestion or a traffic obstruction such as a stop light.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more systems and/or techniques for training and utilizing a traffic obstruction identification model are provided herein. In an example, a training dataset, comprising sample vehicle location points (e.g., individual global positing system (GPS) points, of vehicles traveling along one or more road segments, labeled with vehicle identifiers of corresponding vehicles) and/or traffic obstruction identification labels (e.g., known locations of traffic obstructions such as stop signs, crosswalks, bus stops, etc.), is obtained. A set of training features is extracted from the training dataset based upon the sample vehicle location points (e.g., a portion of vehicles traveling below a threshold speed; a median average deviation in travel time of a vehicle; a point density of sample vehicle location points of a road segment compared to other road segments; etc.). The set of training features are indicative of traffic flow patterns (e.g., stopping patterns, acceleration patterns, speed patterns, a length of a queued line of vehicles, etc.). In an example, the sample vehicle location points may be evaluated as individual points (e.g., as opposed to evaluating trace data where points are connected together, which may otherwise increase processing resource overhead), such that aggregated statistics on individual sample vehicle location points may be used to obtain the set of training features. A traffic obstruction identification model (e.g., a statistical distribution model, a hand constructed parametric model, a neural network that learns from data, or other automatic learning procedure) may be trained using the set of training features to create a trained traffic obstruction identification model, such as to identify parameters for use by the trained traffic obstruction identification model for identifying traffic obstructions based upon vehicle location point data.

The trained traffic obstruction identification model may be used to identify traffic obstructions. For example, a dataset, comprising vehicle location points (e.g., GPS location points of vehicles), may be obtained. The dataset may correspond to one or more road segments for which traffic obstruction classifications are not known (e.g., a lack of information regarding whether a road segment has a crosswalk or not). A set of features may be extracted from the dataset based upon the vehicle location points. The set of features may be indicative of traffic flow patterns (e.g., whether traffic is moving slowly, stopping patterns of vehicles, acceleration patterns of vehicles, a density of vehicles compared to surrounding road segments, a number of vehicles queued in a stopped line of vehicles, etc.). The set of features may be evaluated using the trained traffic obstruction identification model to determine whether a road segment has a traffic obstruction, such as whether the road segment has a stop sign or not. A current traffic flow pattern may be determined as being a result of congestion or from the traffic obstruction based upon whether the road segment has the traffic obstruction or not (e.g., a slow traffic flow may be a result of the stop sign if the road segment comprises the stop sign, otherwise, the slow traffic flow may be merely a result of congestion if the road segment does not comprise the stop sign or other traffic obstructions).

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
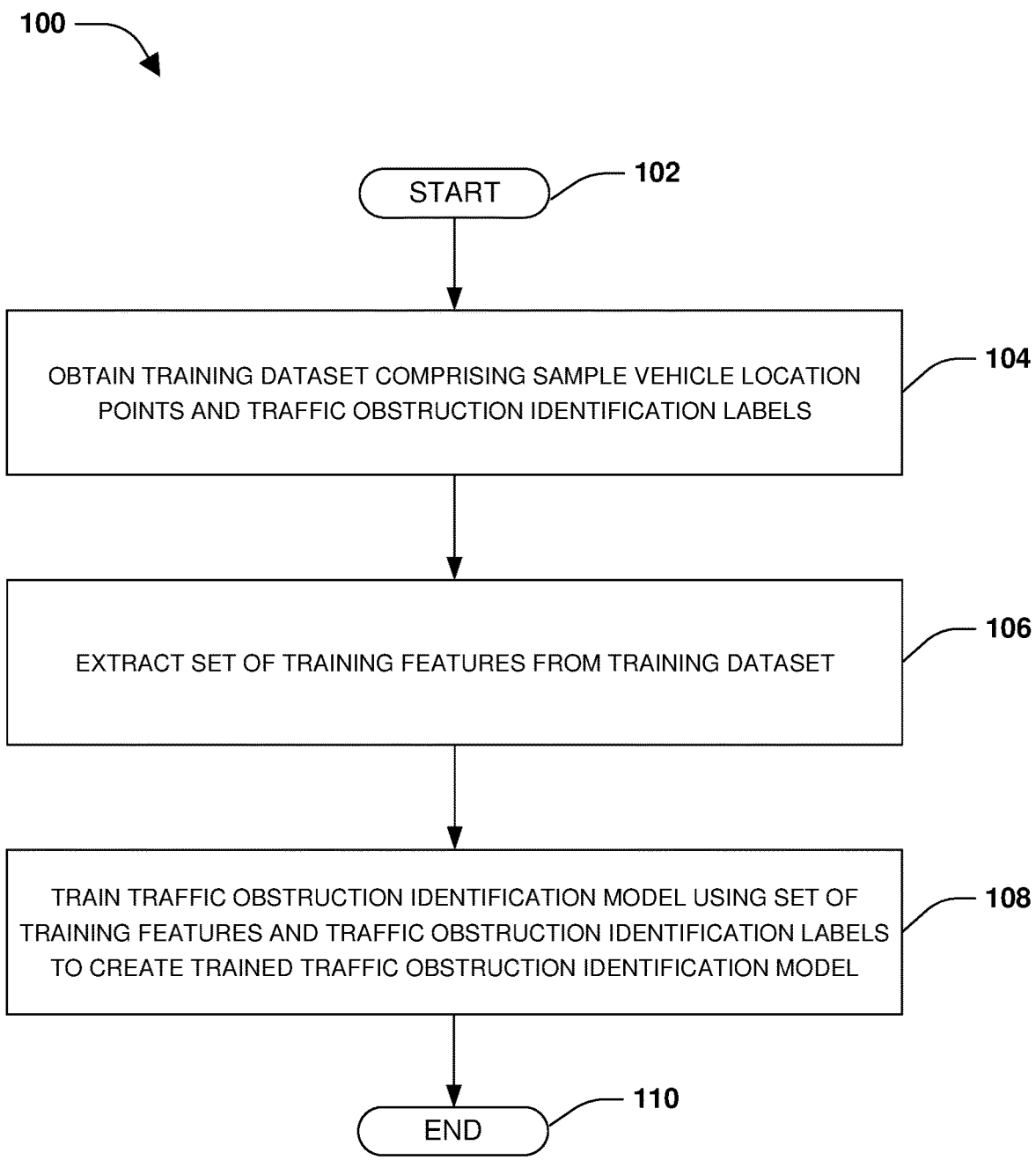
FIG. 1 is a flow diagram illustrating an exemplary method of training a traffic obstruction identification model.

The claimed subject matter is now described with reference to the drawings, wherein like reference numerals are generally used to refer to like elements throughout. In the following description, for purposes of explanation, numerous specific details are set forth to provide an understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for training and/or utilizing a traffic obstruction identification model are provided herein. Users may have a desire to view information that may affect an arrival time to a destination, such as traffic congestion and/or traffic obstructions (e.g., a stop light, a stop sign, a crosswalk, a railroad crossing, a traffic flow impediment, a temporary obstruction (e.g., real-time identification of a temporary traffic light set up to control traffic flow of vehicles near roadwork), a permanent obstruction, etc.). Unfortunately, such information may not be available in map data that is used by navigation route providers to provide users with travel routes (e.g., travel routes provided through a smart phone navigation application, a vehicle navigation system, etc.). As provided herein, patterns in vehicle location points, such as global positioning system (GPS) data, may be used to train a traffic obstruction identification model to create a trained traffic obstruction identification model for identifying locations of traffic obstructions. The trained traffic obstruction identification model may be configured to classify road segments as having traffic obstructions or not by using features (e.g., whether traffic is moving slowly, stopping patterns of vehicles, acceleration patterns of vehicles, a density of vehicles compared to surrounding road segments, a number of vehicles queued in a stopped line of vehicles, etc.) that are independent of a sampling rate of the vehicle location points (e.g., vehicle location points may be collected over a week, a year, etc.). Computational costs of the classification may be reduced because travel times for individual vehicles do not need to be computed and vehicle location points are treated independently (e.g., as opposed to using additional computational resources to track vehicles and/or chain together vehicle location points). In this way, traffic obstructions may be identified so that relatively more accurate travel routes and/or traffic information may be provided to users. For example, a navigation route provider may provide a relatively more accurate travel route and/or travel time that takes into account a traffic obstruction.

An embodiment of training a traffic obstruction identification model is illustrated by an exemplary method 100 of FIG. 1. At 102, the method 100 starts. At 104, a training dataset, comprising sample vehicle location points and traffic obstruction identification labels, may be obtained. The sample vehicle location points may correspond to GPS location points obtained from various vehicles traveling along one or more road segments. A sample vehicle location point may be associated with a vehicle identifier of a vehicle from which the sample vehicle location point originated. The sample vehicle location point may be used to identify an instantaneous speed of the vehicle. The traffic obstruction identification labels may associate known traffic obstructions with road segments (e.g., a location of a known stop sign, crosswalk, railroad crossing, etc.), which may be used to train a traffic obstruction identification model for identifying traffic obstructions.

At 106, a set of training features may be extracted from the training dataset based upon the sample vehicle location points. The set of training features may be indicative of traffic flow patterns (e.g., a first set of training features indicative of traffic flow patterns of a first road segment, a second set of training features indicative of traffic flow patterns of a second road segment, etc.). In an example of extracting a training feature, the sample vehicle location points may be evaluated to identify a count of vehicles having speeds below a speed threshold (e.g., as a vehicle slows down, the vehicle may send vehicle location points that are closer together). The count of vehicles may be compared to a total count of vehicles to determine a vehicle speed feature for inclusion within the set of training features (e.g., a number of slow moving vehicles within a road segment).

In another example of extracting a training feature, the sample vehicle location points are evaluated to determine a median speed of vehicles. A standard deviation from the median speed is identified to determine a median average deviation feature for inclusion within the set of training features (e.g., a median average deviation in kilometer travel time of a vehicle). For example, for respective vehicle location points, a deviation of a vehicle location point (e.g., an instantaneous speed of the vehicle derived from the vehicle location point) from the median speed is identified for inclusion within the median average deviation feature.

In another example of extracting a training feature, a first count of vehicle location points within a first road segment is identified. The first count of vehicle location points is compared to counts of vehicle location points within one or more neighboring road segments to determine a relative point density feature for inclusion within the set of training features. The relative point density feature may indicate what road segments have more vehicles than other road segments, which may be used to identify an end of a queue of vehicles (e.g., an end of a line of vehicles at a stop light) or other traffic flow features. It may be appreciated that while a few training features are discussed herein for illustrative purposes, a variety of training features are contemplated.

At 108, the traffic obstruction identification model is trained using the set of training features and the traffic obstruction identification labels to create a trained traffic obstruction identification model for identifying traffic obstructions based upon vehicle location point data. In an example, if a road segment has a known traffic obstruction (e.g., the traffic obstruction identification labels may indicate that the road segment comprises a railroad crossing), then a training feature of the road segment may be used to train the traffic obstruction identification model to identify such a traffic obstruction (e.g., a railroad crossing) for road segments having a similar feature as the training feature. In another example, if a road segment does not have a known traffic obstruction (e.g., the traffic obstruction identification labels may indicate that the road segment is free of traffic obstructions), then a training feature of the road segment may be used to train the traffic obstruction identification model to determine that road segments having a similar feature as the training feature do not have traffic obstructions. In this way, one or more parameters for use by the trained traffic obstruction identification model may be identified based upon the training dataset and the set of training features. The trained traffic obstruction identification model may be used to identify traffic obstructions and/or for planning relatively more accurate routes that take traffic obstructions into account, as will be further discussed and illustrated in FIGS. 3-5. At 110, the method 100 ends.

Figure 2:
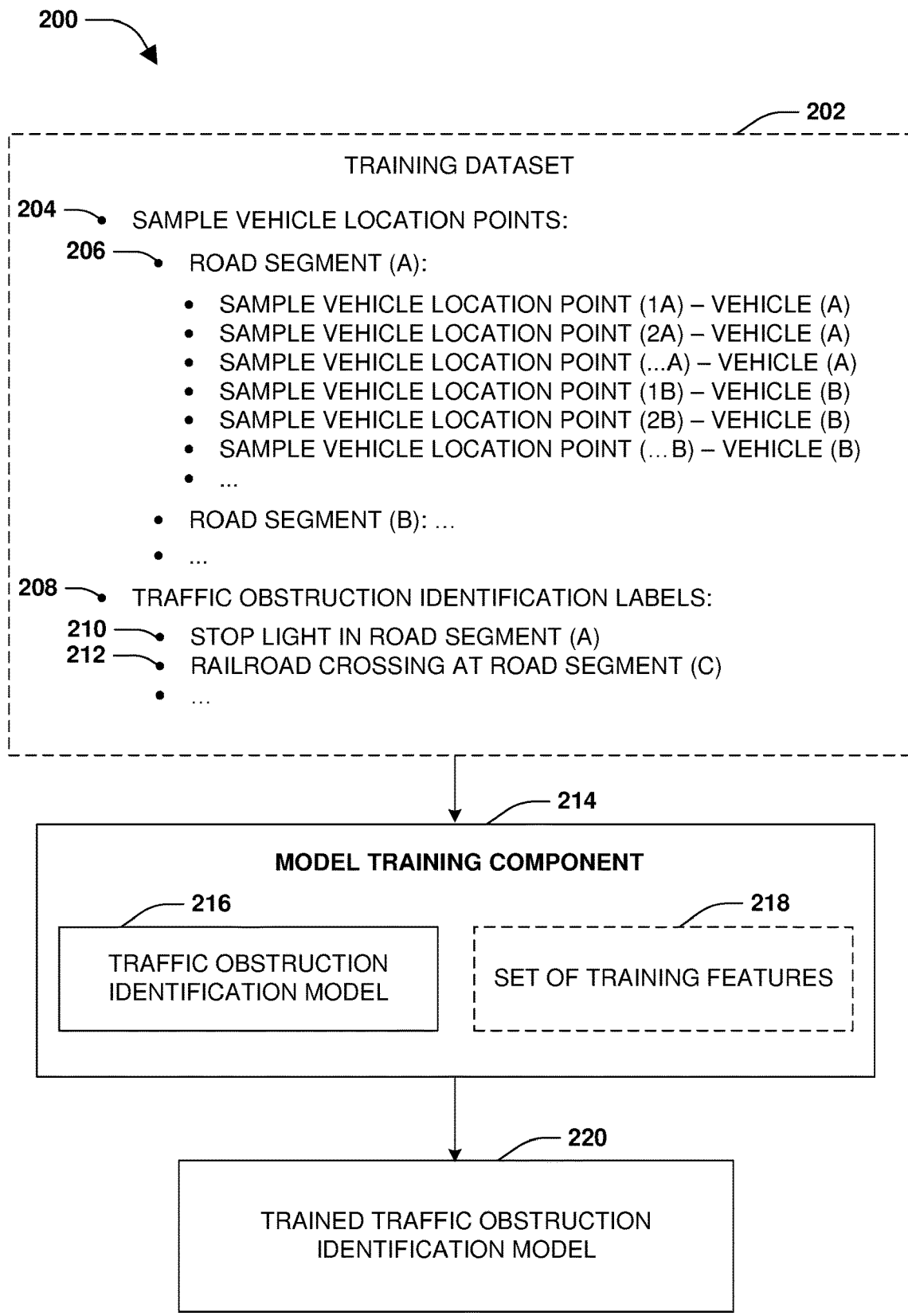
FIG. 2 is a component block diagram illustrating an exemplary system for training a traffic obstruction identification model.

FIG. 2 illustrate an example of a system 200 for training a traffic obstruction identification model 216. The system 200 comprises a model training component 214. The model training component 214 may be configured to obtain a training dataset 202 comprising sample vehicle location points 204 and/or traffic obstruction identification labels 208. For example, the training dataset 202 may comprise sample vehicle location points 204 for a set of road segments, such as a road segment (A) 206, a road segment (B), and/or other road segments (e.g., 100 meter road segments, or any other distance, of a city road in a downtown shopping district of a city). The training dataset 202 may comprise a sample vehicle location point (1A) of a vehicle (A) traveling the road segment (A) 206, a sample vehicle location point (2A) of the vehicle (A) traveling the road segment (A) 206, and/or other sample vehicle location points of the vehicle (A) traveling the road segment (A) 206. The training dataset 202 may comprise a sample vehicle location point (1B) of a vehicle (B) traveling the road segment (A) 206, a sample vehicle location point (2B) of the vehicle (B) traveling the road segment (A) 206, and/or other sample vehicle location points of the vehicle (B) traveling the road segment (A) 206. The training dataset 202 may comprise sample vehicle location points of vehicles traveling the road segment (B) and/or other road segments. A sample vehicle location point may correspond to a GPS location point, of a vehicle, that is transmitted by the vehicle to a data collection service for inclusion within the training dataset 202. Sample vehicle location points may be treated individually (e.g., a training feature may be identified based upon an instantaneous GPS speed derived from a vehicle location point), which may reduce computational costs that may otherwise be incurred from tracking vehicles, chaining vehicle location points together, and/or calculating travel times for individual vehicles.

The traffic obstruction identification labels 208 may comprise locations of known traffic obstructions. For example, the traffic obstruction identification labels 208 may comprise a stop light traffic obstruction identification label 210 specifying that road segment (A) 206 has a stop light traffic obstruction. The traffic obstruction identification labels 208 may comprise a railroad crossing traffic obstruction identification label 212 specifying that a road segment (C) has a railroad crossing traffic obstruction.

The model training component 214 may extract a set of training features 218 from the training dataset 202 based upon the sample vehicle location points 204. For example, the set of training features 218 may comprise a vehicle speed feature, a median average deviation feature, a relative point density feature, and/or a variety of other features that are indicative of traffic flow patterns for the set of road segments. In an example, the set of training features 218 may be independent of a sampling rate of the sample vehicle location points 204. The model training component 214 may train the traffic obstruction identification model 216 using the set of training features 218 and/or the traffic obstruction identification labels 208 to create a trained traffic obstruction identification model 220 for identifying traffic obstructions based upon vehicle location point data. For example, training features of the road segment (A) 206 and/or the stop light traffic obstruction identification label 210 may be used to train the trained traffic obstruction identification model 220 to identify a road segment as having a stop light traffic obstruction based upon the road segment having similar features as the road segment (A) 206 that has the known stop light traffic obstruction. Training features of the road segment (C) and/or the railroad crossing traffic obstruction identification label 212 may be used to train the trained traffic obstruction identification model 220 to identify a road segment as having a railroad crossing traffic obstruction based upon the road segment having similar features as the road segment (C) that has the known railroad crossing traffic obstruction.

Figure 3:
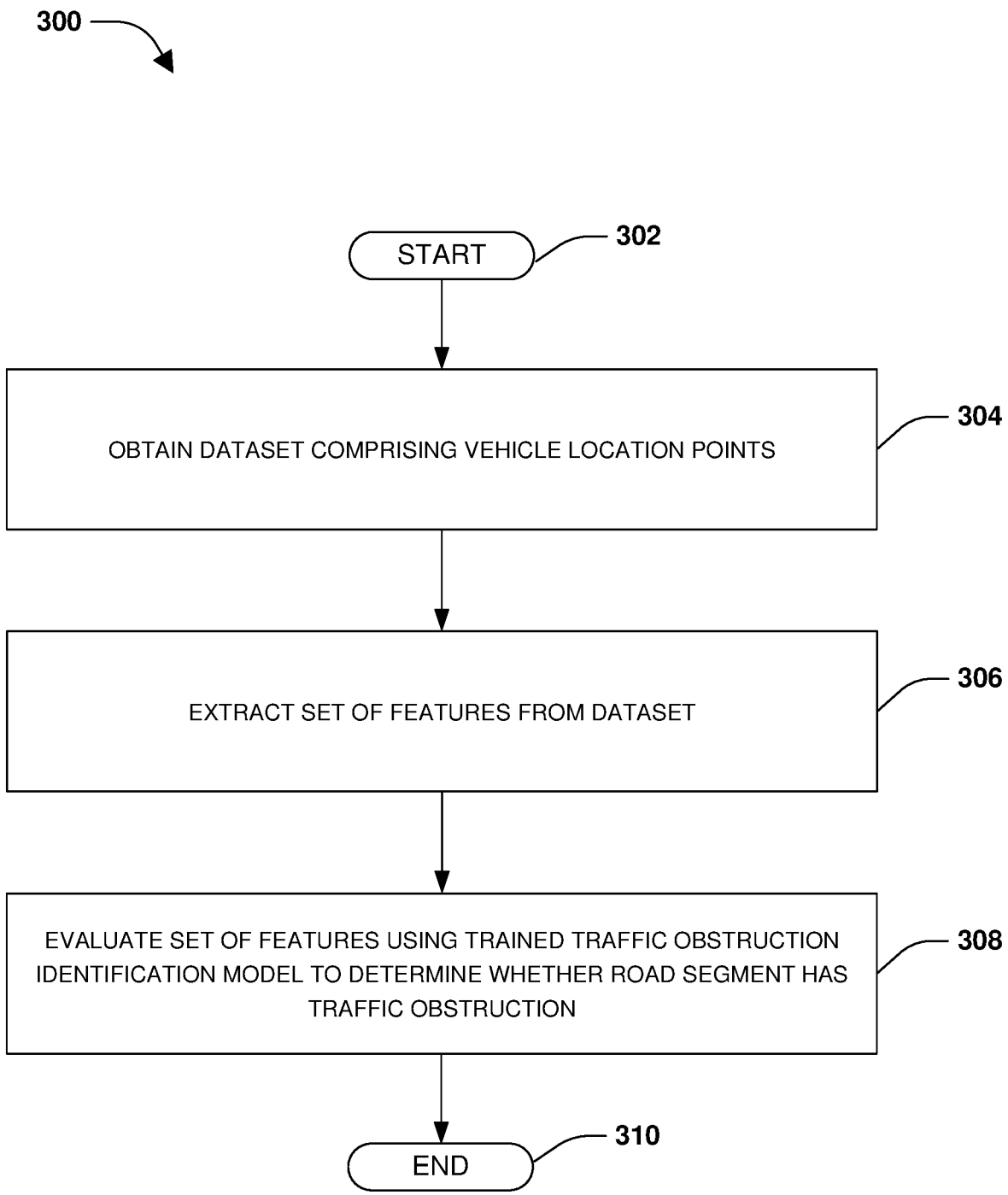
FIG. 3 is a flow diagram illustrating an exemplary method of determining whether a road segment has a traffic obstruction.

An embodiment of determining whether a road segment has a traffic obstruction is illustrated by an exemplary method 300 of FIG. 3. At 302, the method 300 starts. At 304, a dataset, comprising vehicle location points, may be obtained. In an example, one or more vehicles traveling along road segments of a neighborhood road may transmit vehicle location points, such as GPS location points, to a data collection service for inclusion within the dataset. For example, a first set of GPS location points may be received from a first vehicle. A second set of GPS location points may be received from a second vehicle. The first set of GPS location points and the second set of GPS location points may be included within the dataset. In an example, the first set of GPS location points are collected at a first time period (e.g., Monday morning while the first vehicle is driving along a road segment of the neighborhood road) and the second set of GPS location points are collected at a second time period (e.g., Tuesday afternoon while the second vehicle is driving along the road segment of the neighborhood road).

At 306, a set of features may be extracted from the dataset based upon the vehicle location points. For example, the set of features may comprise a vehicle speed feature, a median average deviation feature, a relative point density feature, and/or a variety of other features. The set of features may be indicative of traffic flow patterns (e.g., vehicle stopping patterns, vehicle acceleration patterns, an end of a queued line of vehicles, a distribution and/or density of vehicles along the neighborhood road, vehicle speeds, etc.). In an example, the set of features may be extracted independently from a sampling rate of the dataset (e.g., the dataset may comprise vehicle location points collected over an hour, a week, a year, etc.).

At 308, the set of features may be evaluated using a trained traffic obstruction identification model to determine whether a road segment has a traffic obstruction or not. In an example, the road segment may be classified as having or not having the traffic obstruction based upon values of features within the set of features and one or more parameters of the trained traffic obstruction identification model (e.g., a parameter may indicate that a value of a feature is indicative of a stop sign traffic obstruction or a lack of a stop sign traffic obstruction). In an example, a current traffic flow pattern may be determined as being a result of congestion or the traffic obstruction based upon whether the road segment has the traffic obstruction or not.

In an example, traffic obstructions, such as a temporary traffic obstruction, may be identified in real-time. For example, a set of features may be extracted from a dataset of vehicle location points that are obtained in real-time. The set of features may be evaluated using the trained traffic obstruction identification model to identify a traffic obstruction, such as a temporary traffic light. At 310, the method 300 ends.

Figure 4:
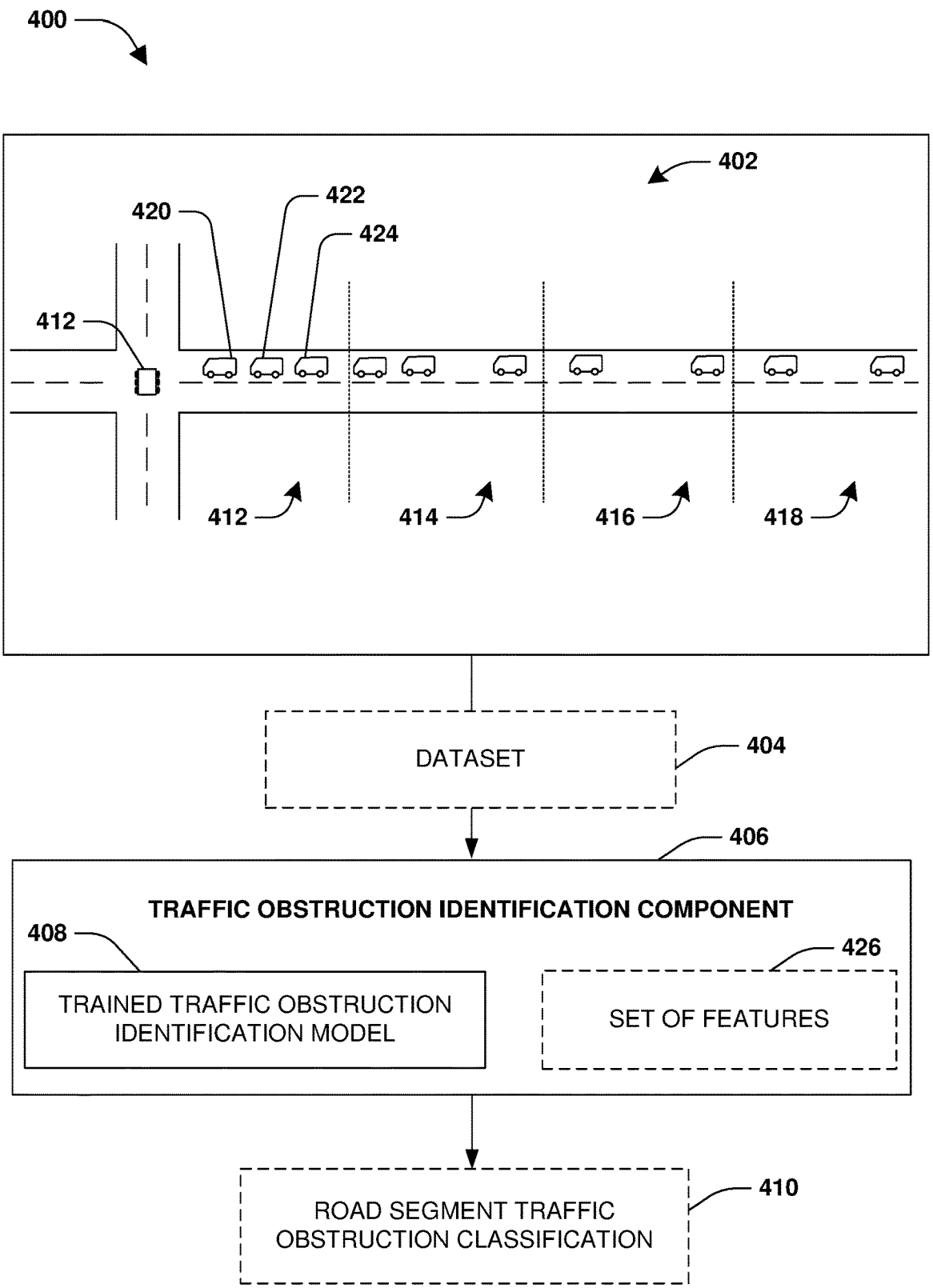
FIG. 4 is a component block diagram illustrating an exemplary system for determining whether a road segment has a traffic obstruction, where the road segment is determined as having the traffic obstruction.

FIG. 4 illustrates an example of a system 400 for determining whether a road segment has a traffic obstruction or not. The system 400 comprises a traffic obstruction identification component 406. The traffic obstruction identification component 406 may be configured to obtain a dataset 404 comprising vehicle location points. The vehicle location points may correspond to GPS location points reported by vehicles traveling along one or more road segments of a road 402, such as a first road segment 412, a second road segment 414, a third road segment 416, a fourth road segment 418, and/or other road segments. For example, a first vehicle 420 may report a first set of GPS location points while traveling along the first road segment 412 and/or other road segments along the road 402. A second vehicle 422 may report a second set of GPS location points while traveling along the first road segment 412 and/or other road segments along the road 402. A third vehicle 424 may report a third set of GPS location points while traveling along the first road segment 412 and/or other road segments along the road 402.

The traffic obstruction identification component 406 may be configured to extract a set of features 426 from the dataset 404. For example, the set of features 426 may comprise a vehicle speed feature, a median average deviation feature, a relative point density feature, and/or a variety of other features. The set of features 426 may be indicative of traffic flow patterns derived from the vehicle location points of the first vehicle 420, the second vehicle 422, the third vehicle 424, and/or other vehicles traveling along the road 402 (e.g., vehicle stopping patterns, vehicle acceleration patterns, an end of a queued line of vehicles, a distribution and/or density of vehicles along the neighborhood road, vehicle speeds, etc.).

The traffic obstruction identification component 406 may be configured to evaluate the set of features 426 using a trained traffic obstruction identification model 408. The trained traffic obstruction identification model 408 may indicate that the set of features 426 may be indicative of the first road segment 412 comprising a stop light traffic obstruction 412. In this way, the traffic obstruction identification component 406 may use the trained traffic obstruction identification model 408 to classify 410 road segments as having or not having traffic obstructions. In an example, a current traffic flow pattern may be determined as being a result of the stop light traffic obstruction 412, as opposed to congestion.

Figure 5:
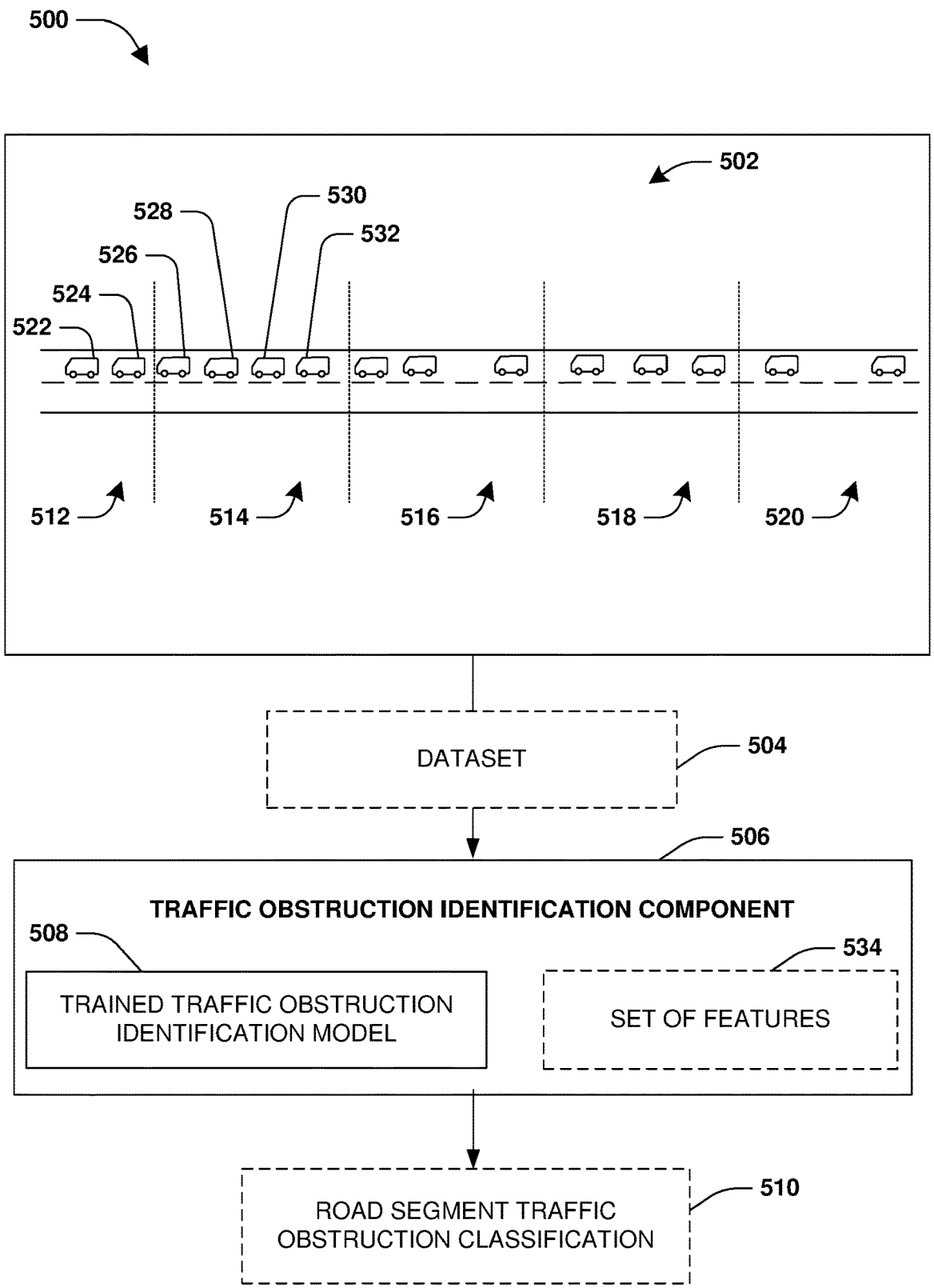
FIG. 5 is a component block diagram illustrating an exemplary system for determining whether a road segment has a traffic obstruction, where the road segment is determined as not having the traffic obstruction.

FIG. 5 illustrates an example of a system 500 for determining whether a road segment has a traffic obstruction or not. The system 500 comprises a traffic obstruction identification component 506. The traffic obstruction identification component 506 may be configured to obtain a dataset 504 comprising vehicle location points. The vehicle location points may correspond to GPS location points reported by vehicles traveling along one or more road segments of a road 502, such as a first road segment 512, a second road segment 514, a third road segment 516, a fourth road segment 518, a fifth road segment 520, and/or other road segments. For example, a first vehicle 522 may report a first set of GPS location points while traveling along the first road segment 512 and/or other road segments along the road 502. A second vehicle 524 may report a second set of GPS location points while traveling along the first road segment 512 and/or other road segments along the road 502. A third vehicle 526 may report a third set of GPS location points while traveling along the second road segment 514 and/or other road segments along the road 502. A fourth vehicle 528 may report a fourth set of GPS location points while traveling along the second road segment 514 and/or other road segments along the road 502. A fifth vehicle 530 may report a fifth set of GPS location points while traveling along the second road segment 514 and/or other road segments along the road 502. A sixth vehicle 532 may report a sixth set of GPS location points while traveling along the second road segment 514 and/or other road segments along the road 502.

The traffic obstruction identification component 506 may be configured to extract a set of features 534 from the dataset 504. For example, the set of features 534 may comprise a vehicle speed feature, a median average deviation feature, a relative point density feature, and/or a variety of other features. The set of features 526 may be indicative of traffic flow patterns derived from the vehicle location points of the first vehicle 522, the second vehicle 524, the third vehicle 526, the fourth vehicle 528, the fifth vehicle 530, the sixth vehicle 532, and/or other vehicles traveling along the road 502 (e.g., vehicle stopping patterns, vehicle acceleration patterns, an end of a queued line of vehicles, a distribution and/or density of vehicles along the neighborhood road, vehicle speeds, etc.).

The traffic obstruction identification component 506 may be configured to evaluate the set of features 534 using a trained traffic obstruction identification model 508. The trained traffic obstruction identification model 508 may indicate that the set of features 534 may be indicative of the road 502 not comprising a traffic obstruction. In this way, the traffic obstruction identification component 506 may use the trained traffic obstruction identification model 508 to classify 510 road segments as having or not having traffic obstructions. In an example, a current traffic flow pattern may be determined as being a result of congestion because the road 502 does not comprise traffic obstructions and the set of features 534 are indicative of a slow traffic flow.

Figure 6:
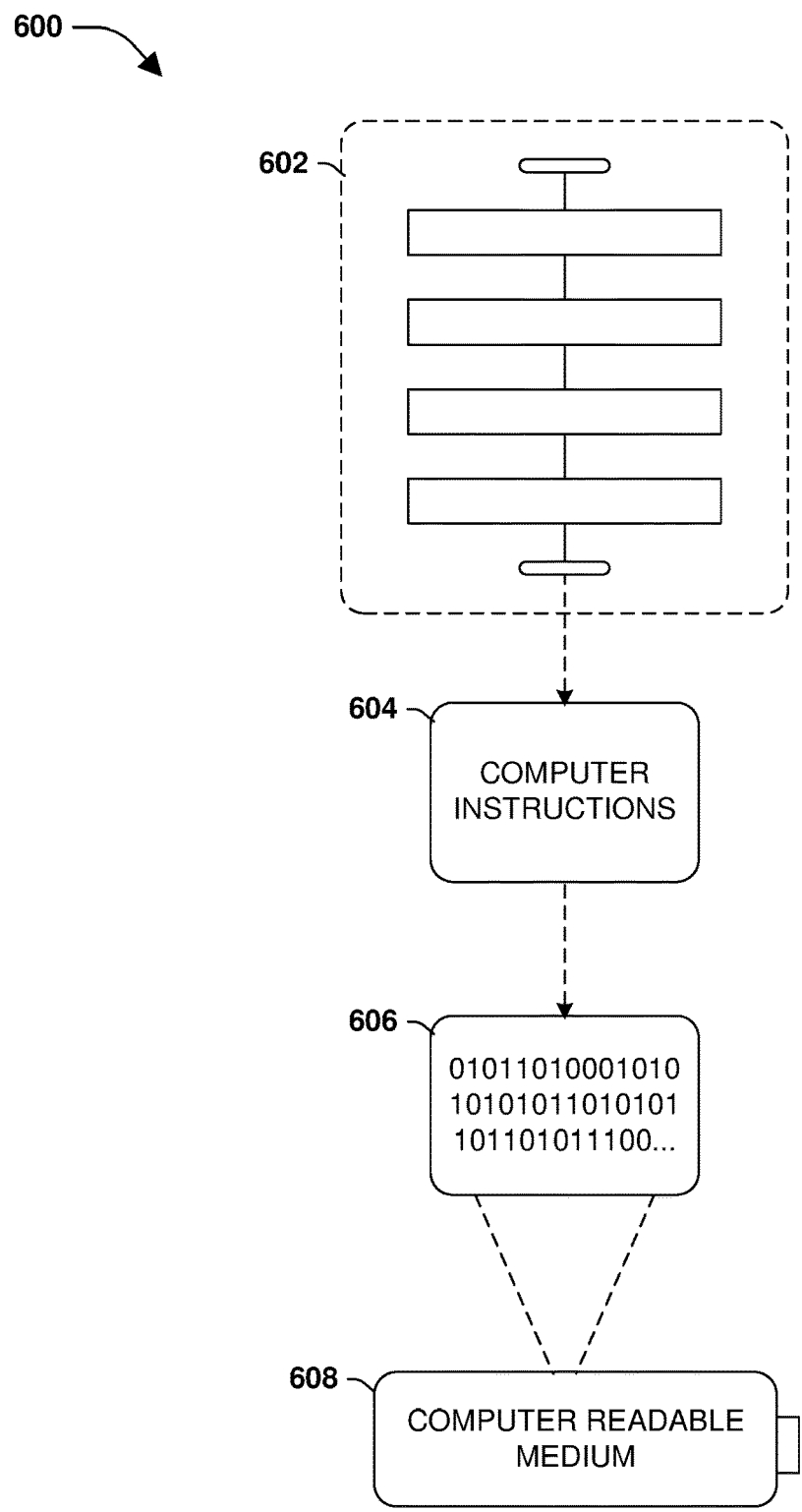
FIG. 6 is an illustration of an exemplary computer readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device is illustrated in FIG. 6, wherein the implementation 600 comprises a computer-readable medium 608, such as a CD-R, DVD-R, flash drive, a platter of a hard disk drive, etc., on which is encoded computer-readable data 606. This computer-readable data 606, such as binary data comprising at least one of a zero or a one, in turn comprises a set of computer instructions 604 configured to operate according to one or more of the principles set forth herein. In some embodiments, the set of computer instructions 604 are configured to perform a method 602, such as at least some of the exemplary method 100 of FIG. 1 and/or at least some of the exemplary method 300 of FIG. 3, for example. In some embodiments, the set of computer instructions 604 are configured to implement a system, such as at least some of the exemplary system 200 of FIG. 2, at least some of the exemplary system 400 of FIG. 4, and/or at least some of the exemplary system 500 of FIG. 5, for example. Many such computer-readable media are devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

As used in this application, the terms "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 7:
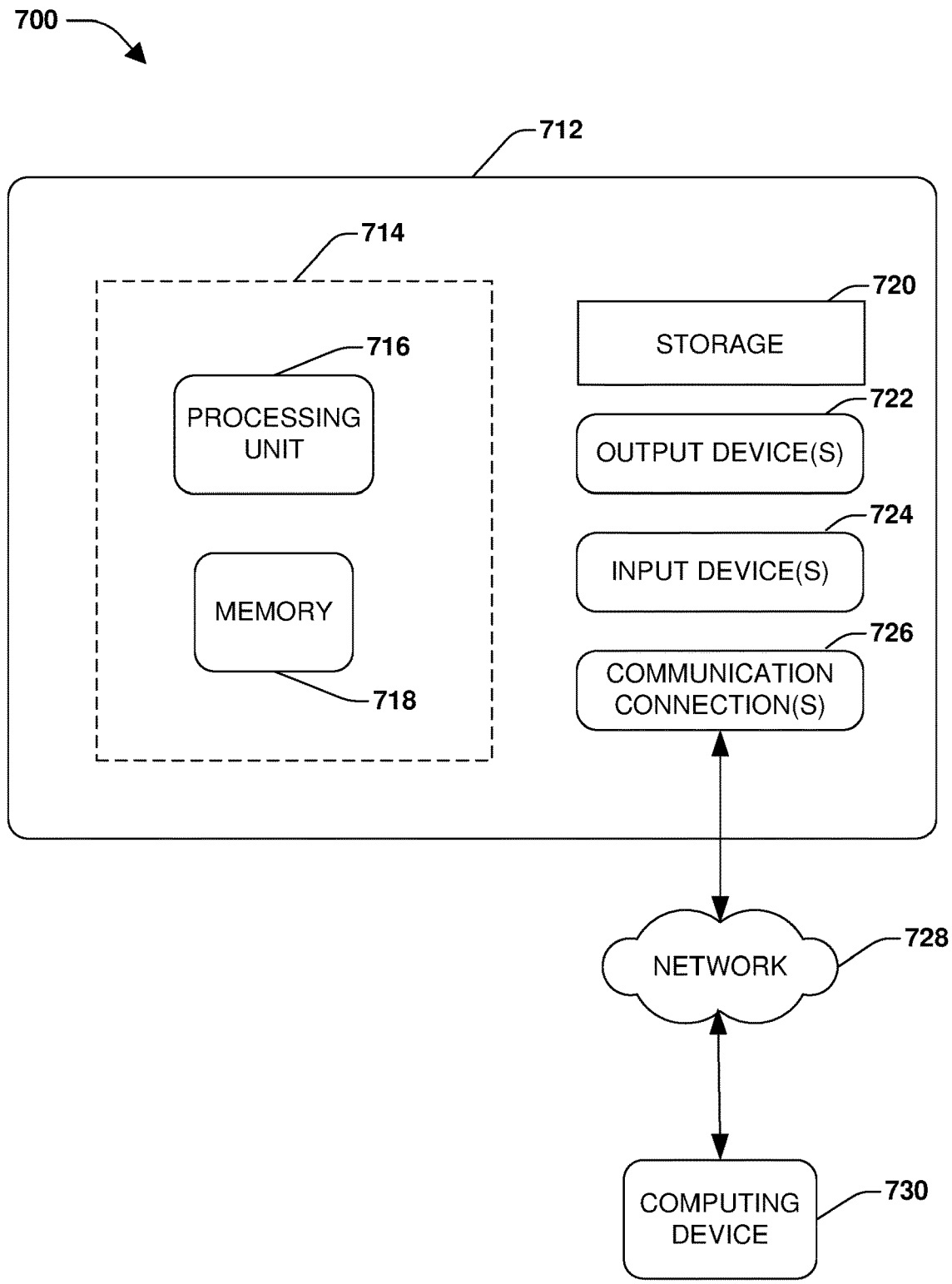
FIG. 7 illustrates an exemplary computing environment wherein one or more of the provisions set forth herein may be implemented.

FIG. 7 and the following discussion provide a brief, general description of a suitable computing environment to implement embodiments of one or more of the provisions set forth herein. The operating environment of FIG. 7 is only one example of a suitable operating environment and is not intended to suggest any limitation as to the scope of use or functionality of the operating environment. Example computing devices include, but are not limited to, personal computers, server computers, hand held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 7 illustrates an example of a system 700 comprising a computing device 712 configured to implement one or more embodiments provided herein. In one configuration, computing device 712 includes at least one processing unit 716 and memory 718. Depending on the exact configuration and type of computing device, memory 718 may be volatile (such as RAM, for example), non-volatile (such as ROM, flash memory, etc., for example) or some combination of the two. This configuration is illustrated in FIG. 7 by dashed line 714.

In other embodiments, device 712 may include additional features and/or functionality. For example, device 712 may also include additional storage (e.g., removable and/or non-removable) including, but not limited to, magnetic storage, optical storage, and the like. Such additional storage is illustrated in FIG. 7 by storage 720. In one embodiment, computer readable instructions to implement one or more embodiments provided herein may be in storage 720. Storage 720 may also store other computer readable instructions to implement an operating system, an application program, and the like. Computer readable instructions may be loaded in memory 718 for execution by processing unit 716, for example.

The term "computer readable media" as used herein includes computer storage media. Computer storage media includes volatile and nonvolatile, removable and non-removable media implemented in any method or technology for storage of information such as computer readable instructions or other data. Memory 718 and storage 720 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 712. Computer storage media does not, however, include propagated signals. Rather, computer storage media excludes propagated signals. Any such computer storage media may be part of device 712.

Device 712 may also include communication connection(s) 726 that allows device 712 to communicate with other devices. Communication connection(s) 726 may include, but is not limited to, a modem, a Network Interface Card (NIC), an integrated network interface, a radio frequency transmitter/receiver, an infrared port, a USB connection, or other interfaces for connecting computing device 712 to other computing devices. Communication connection(s) 726 may include a wired connection or a wireless connection. Communication connection(s) 726 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 712 may include input device(s) 724 such as keyboard, mouse, pen, voice input device, touch input device, infrared cameras, video input devices, and/or any other input device. Output device(s) 722 such as one or more displays, speakers, printers, and/or any other output device may also be included in device 712. Input device(s) 724 and output device(s) 722 may be connected to device 712 via a wired connection, wireless connection, or any combination thereof. In one embodiment, an input device or an output device from another computing device may be used as input device(s) 724 or output device(s) 722 for computing device 712.

Components of computing device 712 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 712 may be interconnected by a network. For example, memory 718 may be comprised of multiple physical memory units located in different physical locations interconnected by a network.

Those skilled in the art will realize that storage devices utilized to store computer readable instructions may be distributed across a network. For example, a computing device 730 accessible via a network 728 may store computer readable instructions to implement one or more embodiments provided herein. Computing device 712 may access computing device 730 and download a part or all of the computer readable instructions for execution. Alternatively, computing device 712 may download pieces of the computer readable instructions, as needed, or some instructions may be executed at computing device 712 and some at computing device 730.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, or is intended to mean an inclusive "or" rather than an exclusive "or". In addition, "a" and "an" as used in this application are generally be construed to mean one or more unless specified otherwise or clear from context to be directed to a singular form. Also, at least one of A and B and/or the like generally means A or B and/or both A and B. Furthermore, to the extent that "includes", "having", "has", "with", and/or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for training a traffic obstruction identification model, comprising:
    obtaining a training dataset comprising sample vehicle location points and traffic obstruction identification labels, wherein the traffic obstruction identification labels correspond to traffic obstructions configured to control a flow of traffic and disposed at fixed locations along road segments;
    extracting a set of training features from the training dataset based upon the sample vehicle location points, the set of training features indicative of traffic flow patterns, the traffic flow patterns indicative of a flow of traffic along a first set of one or more road segments; and
    training a traffic obstruction identification model using the set of training features and the traffic obstruction identification labels to create a trained traffic obstruction identification model for identifying other traffic obstructions along a second set of one or more road segments different than the first set of one or more road segments based upon traffic flow patterns of vehicles encountering the other traffic obstructions along the second set of one or more road segments, the training a traffic obstruction identification model comprising:
        training the traffic obstruction identification model using the set of training features and the traffic obstruction identification labels to create the trained traffic obstruction identification model to identify a first traffic obstruction as being present on a first road segment of the second set of one or more road segments when a traffic flow pattern of the first road segment matches a traffic flow pattern of a second road segment of the first set of one or more road segments having the first traffic obstruction; and
        training the traffic obstruction identification model using the set of training features and the traffic obstruction identification labels to create the trained traffic obstruction identification model to identify a second traffic obstruction as being present on a third road segment of the second set of one or more road segments when a traffic flow pattern of the third road segment matches a traffic flow pattern of a fourth road segment of the first set of one or more road segments having the second traffic obstruction.

2. The method of claim 1, the traffic obstructions comprising at least one of a stop light, a stop sign, a crosswalk, or a railroad crossing.

3. The method of claim 1, the extracting a set of training features comprising:
    evaluating the sample vehicle location points to identify a count of vehicles having speeds below a speed threshold; and
    comparing the count of vehicles to a total count of vehicles to determine a vehicle speed feature for inclusion within the set of training features.

4. The method of claim 1, the extracting a set of training features comprising:
    evaluating the sample vehicle location points to determine a median speed; and
    identifying a standard deviation from the median speed to determine a median average deviation feature for inclusion within the set of training features.

5. The method of claim 1, the extracting a set of training features comprising:
    identifying a first count of vehicle location points within a fifth road segment; and
    comparing the first count of vehicle location points to counts of vehicle location points within one or more neighboring road segments to determine a relative point density feature for inclusion within the set of training features.

6. The method of claim 1, the training a traffic obstruction identification model comprising:
    identifying one or more parameters for use by the trained traffic obstruction identification model based upon the training dataset and the set of training features.

7. The method of claim 1, the extracting a set of training features comprising:
- extracting a first set of training features for the second road segment of the first set of one or more road segments and associated with the first traffic obstruction of the traffic obstructions; and
- extracting a second set of training features for the fourth road segment of the first set of one or more road segments and associated with the second traffic obstruction of the traffic obstructions, the second traffic obstruction different than the first traffic obstruction.

8. A system for training a traffic obstruction identification model, comprising:
- a model training component configured to:
  - obtain a training dataset comprising sample vehicle location points and traffic obstruction identification labels, wherein the traffic obstruction identification labels correspond to traffic obstructions configured to control a flow of traffic and disposed at fixed locations along road segments;
  - extract a set of training features from the training dataset based upon the sample vehicle location points, the set of training features indicative of traffic flow patterns, the traffic flow patterns indicative of a flow of traffic along a first set of one or more road segments; and
  - train a traffic obstruction identification model using the set of training features and the traffic obstruction identification labels to create a trained traffic obstruction identification model for identifying other traffic obstructions along a second set of one or more road segments different than the first set of one or more road segments based upon traffic flow patterns of vehicles encountering the other traffic obstructions along the second set of one or more road segments, wherein training the traffic obstruction identification model comprises:
    - training the traffic obstruction identification model using the set of training features and the traffic obstruction identification labels to create the trained traffic obstruction identification model to identify a first traffic obstruction as being present on a first road segment of the second set of one or more road segments when a traffic flow pattern of the first road segment matches a traffic flow pattern of a second road segment of the first set of one or more road segments having the first traffic obstruction; and
    - training the traffic obstruction identification model using the set of training features and the traffic obstruction identification labels to create the trained traffic obstruction identification model to identify a second traffic obstruction as being present on a third road segment of the second set of one or more road segments when a traffic flow pattern of the third road segment matches a traffic flow pattern of a fourth road segment of the first set of one or more road segments having the second traffic obstruction.

9. The system of claim 8, wherein the traffic flow patterns comprise at least one of:
- a stopping pattern along at least one road segment of the first set of one or more road segments,
- an acceleration pattern along the at least one road segment of the first set of one or more road segments,
- a speed pattern along the at least one road segment of the first set of one or more road segments, or
- a length of a queued line of vehicles along the at least one road segment of the first set of one or more road segments.

10. The method of claim 1, wherein the traffic flow patterns comprise a stopping pattern along at least one road segment of the first set of one or more road segments.

11. The method of claim 1, wherein the traffic flow patterns comprise an acceleration pattern along at least one road segment of the first set of one or more road segments.

12. The method of claim 1, wherein the traffic flow patterns comprise a speed pattern along at least one road segment of the first set of one or more road segments.

13. The method of claim 1, wherein the traffic flow patterns comprise a length of a queued line of vehicles along at least one road segment of the first set of one or more road segments.

14. A computer readable medium comprising instructions which when executed perform a method for training a traffic obstruction identification model, comprising:
- obtaining a training dataset comprising sample vehicle location points and traffic obstruction identification labels, wherein the traffic obstruction identification labels correspond to traffic obstructions configured to control a flow of traffic and disposed at fixed locations along road segments;
- extracting a set of training features from the training dataset based upon the sample vehicle location points, the set of training features indicative of traffic flow patterns, the traffic flow patterns indicative of a flow of traffic along a first set of one or more road segments; and
- training a traffic obstruction identification model using the set of training features and the traffic obstruction identification labels to create a trained traffic obstruction identification model for identifying other traffic obstructions along a second set of one or more road segments different than the first set of one or more road segments based upon traffic flow patterns of vehicles encountering the other traffic obstructions along the second set of one or more road segments, the training a traffic obstruction identification model comprising:
  - training the traffic obstruction identification model using the set of training features and the traffic obstruction identification labels to create the trained traffic obstruction identification model to identify a first traffic obstruction as being present on a first road segment of the second set of one or more road segments when a traffic flow pattern of the first road segment matches a traffic flow pattern of a second road segment of the first set of one or more road segments having the first traffic obstruction; and
  - training the traffic obstruction identification model using the set of training features and the traffic obstruction identification labels to create the trained traffic obstruction identification model to identify a second traffic obstruction as being present on a third road segment of the second set of one or more road segments when the traffic flow pattern of a third road segment matches a traffic flow pattern of a fourth road segment of the first set of one or more road segments having the second traffic obstruction.

15. The computer readable medium of claim 14, the traffic obstructions comprising at least one of a stop light, a stop sign, a crosswalk, or a railroad crossing.

16. The computer readable medium of claim 14, the extracting a set of training features comprising:
- evaluating the sample vehicle location points to identify a count of vehicles having speeds below a speed threshold; and
- comparing the count of vehicles to a total count of vehicles to determine a vehicle speed feature for inclusion within the set of training features.

17. The computer readable medium of claim 14, the extracting a set of training features comprising:
- evaluating the sample vehicle location points to determine a median speed; and
- identifying a standard deviation from the median speed to determine a median average deviation feature for inclusion within the set of training features.

18. The computer readable medium of claim 14, the extracting a set of training features comprising:
- identifying a first count of vehicle location points within a fifth road segment; and
- comparing the first count of vehicle location points to counts of vehicle location points within one or more neighboring road segments to determine a relative point density feature for inclusion within the set of training features.

19. The computer readable medium of claim 14, the training a traffic obstruction identification model comprising:
- identifying one or more parameters for use by the trained traffic obstruction identification model based upon the training dataset and the set of training features.

20. The computer readable medium of claim 14, the extracting a set of training features comprising:
- extracting a first set of training features for the second road segment of the first set of one or more road segments and associated with the first traffic obstruction of the traffic obstructions; and
- extracting a second set of training features for the fourth road segment of the first set of one or more road segments and associated with the second traffic obstruction of the traffic obstructions, the second traffic obstruction different than the first traffic obstruction.

* * * * *